US00PP28726P2

(12) United States Plant Patent
Damsted

(10) Patent No.: US PP28,726 P2
(45) Date of Patent: Dec. 5, 2017

(54) ***PITTOSPORUM* PLANT NAMED 'PITTLB2'**

(50) Latin Name: *Pittosporum tenuifolium*
Varietal Denomination: PITTLB2

(71) Applicant: Morten Damsted, Kaiwaka (NZ)

(72) Inventor: Morten Damsted, Kaiwaka (NZ)

( * ) Notice: Subject to any disclaimer, the term of this patent is extended or adjusted under 35 U.S.C. 154(b) by 0 days.

(21) Appl. No.: 15/330,702

(22) Filed: Oct. 28, 2016

(51) Int. Cl.
*A01H 5/00* (2006.01)

(52) U.S. Cl.
USPC ..... Plt./234

(58) Field of Classification Search
USPC ..... Plt./234, 226
CPC ..... A01H 5/00
See application file for complete search history.

*Primary Examiner* — Kent L Bell

(57) ABSTRACT

A new cultivar of *Pittosporum* plant named 'PITTLB2' that is characterized by a a spherical shape, small overall size, a compact habit and oval shaped leaves that are green in color.

1 Drawing Sheet

Botanical classification: *Pittosporum tenuifolium.*
Variety denomination: 'PITTLB2'.

BACKGROUND OF THE INVENTION

The present invention relates to a new and distinct cultivar of *Pittosporum* plant botanically known as *Pittosporum tenuifolium* and hereinafter referred to by the cultivar name 'PITTLB2'.

The new cultivar was discovered by the inventor in a cultivated area of Whenuapai, New Zealand in 2012. 'PITTLB2' was discovered as a naturally occurring branch mutation of *Pittosporum* 'Little Burger' (not patented).

Asexual reproduction by cuttings of the new cultivar 'PITTLB2' was first performed in 2012 in Whenuapai, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Pittosporum* cultivar 'PITTLB2'.

1. *Pittosporum* 'PITTLB2' exhibits a spherical shape and small overall size.
2. *Pittosporum* 'PITTLB2' exhibits a compact habit.
3. *Pittosporum* 'PITTLB2' exhibits oval shaped leaves that are green in color.

The closest comparison cultivar is the parent plant *Pittosporum* 'Little Burger'. The new cultivar 'PITTLB2' is distinguishable from 'Little Burger' by the following characteristics:

1. 'PITTLB2' exhibits oval shaped leaves that are longer in length than the leaves of 'Little Burger'.
2. 'PITTLB2' exhibits green leaves. In comparison, the leaves of 'Little Burger' are lighter green in color.
3. 'PITTLB2' exhibits branches with internodes that are shorter than the internodes of 'Little Burger'.

BRIEF DESCRIPTION OF THE DRAWING

The accompanying photograph illustrates the distinguishing traits of *Pittosporum* 'PITTLB2'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Pittosporum* cultivar named 'PITTLB2'. Data was collected in Whenuapai, New Zealand from 12 month old outdoor grown plants in 2.5 liter containers. The time of year was Spring in the Southern Hemisphere and the average temperature range was 10 to 25 degrees Centigrade during the day and 5 to 12 degrees Centigrade at night. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'PITTLB2' has not been tested under all possible conditions and phenotypic differences may be observed with variations in environmental, climatic, and cultural conditions, however, without any variance in genotype.

Botanical classification: *Pittosporum tenuifolium* 'PITTLB2'.
Use: Ornamental perennial.
Parentage: 'PITTLB2' is a naturally occurring branch mutation of *Pittosporum* 'Little Burger'.
Vigor: Moderate.
Growth rate: Fast.
Growth habit: Freely branching, dense, bushy habit.
Plant shape: Spherical, compact.
Suitable container size: 2.5 liter container.
Height: Average 70 cm. in height.
Width: Average 100 cm. in width.
Low temperature tolerance: −4 degrees Centigrade.
High temperature tolerance: 38 degrees Centigrade.
Propagation: Cuttings.
Time to initiate roots: Approximately 16 days in the Summer at 23 degrees Centigrade and 20 days in the Winter at 18 degrees Centigrade.

Time to produce a rooted cutting: Approximately 90 days in the Summer at 23 degrees Centigrade and 120 days in the Winter at 18 degrees Centigrade.

Root system: Fine and fibrous.

Lateral branches:

*Quantity*.—Approximately 32.

*Dimensions*.—Average 45.0 cm. in length and 4.4 mm. in diameter.

*Internode length*.—Average 7.4 mm.

*Stem color*.—N199.

*Stem pubescence*.—Absent.

*Stem texture*.—Glabrous, with sparse lenticels.

*Stem luster*.—Dull.

*Strength*.—Strong.

*Pinching*.—No.

Foliage:

*Leaf arrangement*.—Alternate.

*Leaf attachment*.—Petiolate.

*Compound or single*.—Single.

*Quantity of leaves per lateral branch*.—Approximately 12.

*Leaf shape*.—Oval.

*Leaf apex*.—Acute.

*Leaf base*.—Rounded.

*Leaf length*.—Average 3.4 cm. in length.

*Leaf width*.—Average 1.7 cm. in width.

*Texture*.—Smooth (both surfaces).

*Luster*.—Glossy (both surfaces).

*Pubescence*.—Absent.

*Leaf margin*.—Entire, undulate.

*Vein pattern*.—Pinnate.

*Young leaf color* (*upper surface*).—146A.

*Young leaf color* (*lower surface*).—148B.

*Mature leaf color* (*upper surface*).—146A.

*Mature leaf color* (*lower surface*).—147B.

*Vein color* (*upper surface*).—147C.

*Vein color* (*lower surface*).—147D.

*Durability of foliage to stress*.—Moderate to high.

Petiole:

*Dimensions*.—Average 6.0 mm. in length and 1.2 mm. in diameter.

*Texture*.—Glabrous.

*Color*.—147C.

Flowers: *Pittosporum* 'PITTLB2' has not produced flowers to date.

Fruit and seed: *Pittosporum* 'PITTLB2' has not produced fruit or seed to date.

Disease and insect resistance: Plants of the new *Pittosporum* have not been observed for disease or insect resistance to date.

The invention claimed is:

1. A new and distinct variety of *Pittosporum* plant named 'PITTLB2' as described and illustrated.

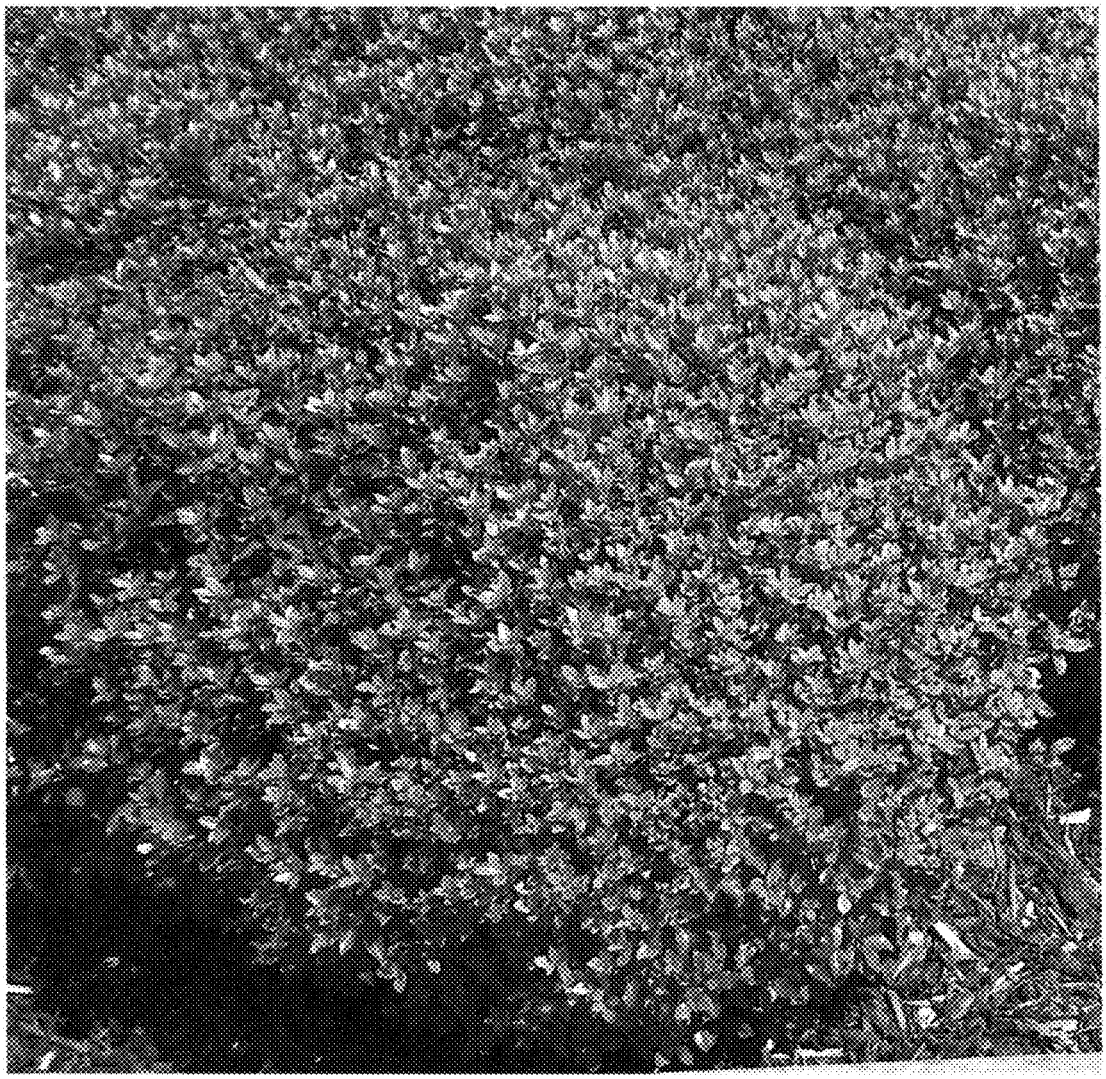

* * * * *